United States Patent [19]

Neti

[11] Patent Number: 4,575,410
[45] Date of Patent: Mar. 11, 1986

[54] SOLID STATE ELECTRODE SYSTEM FOR MEASURING PH

[75] Inventor: Radhakrishna M. Neti, Brea, Calif.

[73] Assignee: Beckman Industrial Corporation, Cedar Grove, N.J.

[21] Appl. No.: 621,890

[22] Filed: Jun. 19, 1984

Related U.S. Application Data

[63] Continuation of Ser. No. 357,221, Mar. 11, 1982, abandoned.

[51] Int. Cl.[4] ............................................. G01N 27/56
[52] U.S. Cl. ................................... 204/422; 204/1 T; 204/433; 204/435
[58] Field of Search .............................. 204/419–421, 204/424–429, 433, 435, 1 T, 1 H

[56] References Cited

U.S. PATENT DOCUMENTS

| | | | |
|---|---|---|---|
| 2,117,596 | 5/1938 | Bender et al. | 204/420 |
| 2,925,370 | 2/1960 | Rohrer | 204/435 |
| 3,282,817 | 11/1966 | Riseman et al. | 204/420 |
| 3,619,381 | 11/1971 | Fitterer | 204/423 |
| 3,649,506 | 3/1972 | Petersen et al. | 204/420 |
| 3,719,564 | 3/1973 | Lilly et al. | 204/426 |
| 3,787,307 | 1/1974 | Schwab et al. | 204/420 |
| 3,853,731 | 12/1974 | Gray et al. | 204/420 |
| 4,002,547 | 1/1977 | Neti et al. | 204/435 |
| 4,040,929 | 8/1977 | Bauer et al. | 204/426 |
| 4,062,750 | 12/1977 | Butler | 204/415 |
| 4,133,735 | 1/1979 | Afromowitz et al. | 204/420 |
| 4,166,009 | 8/1979 | Fray | 204/422 |
| 4,211,624 | 7/1980 | Semkina et al. | 204/422 |
| 4,214,968 | 7/1980 | Battaglia et al. | 204/418 |
| 4,256,561 | 3/1981 | Schindler et al. | 204/418 |
| 4,264,424 | 4/1981 | Niedrach | 204/433 |
| 4,280,889 | 7/1981 | Szonntagh | 204/420 |
| 4,328,082 | 5/1982 | Neti et al. | 204/420 |
| 4,406,766 | 9/1983 | MacDonald | 204/422 |

OTHER PUBLICATIONS

"RF Sputtering of Insulator Films Offers Many Advantages", P. Davidse et al, *Insulation*, Apr. 1966, pp. 41 ff.

*Primary Examiner*—T. Tung
*Attorney, Agent, or Firm*—Daniel H. Bobis

[57] ABSTRACT

An improved solid state electrode system for measuring the pH of fluids at temperatures as high or even higher than that corresponding to the critical point of water (374.2° C.). A stabilized metal oxide based ceramic member having a predetermined thickness is coupled to a first metallic conductor by a uniform, solid oxygen-free electrolyte to serve as a pH sensing electrode. A body of an electrochemically inert material, which preferably comprises a stabilized metal oxide based ceramic member having a lesser thickness or a greater porosity, is coupled to a second metallic conductor by a similar uniform solid electrolyte to serve as a reference electrode. Together the pH and reference electrodes form an electrode system that is suitable for use in applications in which the temperatures and/or pressures of the test solution preclude the use of conventional electrodes. A variety of configurations and compositions are disclosed which allow the electrode system to be fabricated in an improved manner.

1 Claim, 14 Drawing Figures

SOLID STATE ELECTRODE SYSTEM FOR MEASURING PH

This is a continuation of co-pending application Ser. No. 357,221 filed on Mar. 11, 1982, now abandoned.

BACKGROUND OF THE INVENTION

In applications in which the pH of a test solution is to be measured potentiometrically, one of the earliest and still widely used types of electrode systems is based on the use of a glass electrode. This type of electrode system usually includes a pH sensitive glass member that is filled with a suitable electrolyte solution, such as potassium chloride in water, in which is immersed a suitable internal reference, such as a silver wire that has been coated with a layer of silver chloride. This type of electrode system also includes a reference electrode comprising a closed body member that is filled with an electrolyte solution, such as potassium chloride in water, in which is immersed an internal reference similar to that used in the pH electrode. Unlike the pH electrode, however, the reference electrode also includes a leak structure or liquid junction for establishing ionic continuity between its internal electrolyte and the test solution. One representative glass pH electrode structure is shown in U.S. Pat. No. 2,256,733, issued in the name of Cary et al. on Sept. 23, 1941. One representative reference electrode structure, which is based on the use of a glass body member, is shown in U.S. Pat. No. 2,925,370, issued in the name of Rohrer on Feb. 16, 1960.

One problem with glass electrodes of both types is the fact that the properties of the internal electrolyte solution can change with time. In pH electrodes, for example, slow evaporation, and/or condensation, the growth of microbes and other influences can result in changes in the activity of the electrolyte. In reference electrodes, on the other hand, diffusion through the liquid junction gives rise not only to changes in the concentration of the electrolyte, but also to cross-contamination of the electrolyte and test solutions.

In dealing with the above problems, various pH electrodes have been designed to operate with solid electrolytes. One example of a pH electrode with a solid electrolyte is shown in U.S. Pat. No. 3,853,731, issued in the name of Gray et al. on Dec. 10, 1974. Another pH electrode of this type is shown in U.S. Pat. No. 4,062,750, issued in the name of Butler on Dec. 13, 1977. A more recent pH electrode of this type is described in my copending application Ser. No. 163,112 filed June 26, 1980. Except in the latter instance, however, these solid electrolyte systems comprise non-uniform structures, i.e., structures which are deposited in a succession of layers.

Attempts have also been made to design reference electrodes having solid electrolytes. One reference electrode of this type is shown in U.S. Pat. No. 4,280,889, issued in the name of Szonntagh on July 28, 1981. Another electrode of this type is shown in the above-cited Butler patent.

In spite of the benefits resulting from the use of dry solid electrolytes, pH and reference electrodes that use glass body materials can only be used with test solutions at relatively low temperatures, particularly in test solutions that are strongly alkaline. This is because at pH's in excess of approximately 11 and temperatures in excess of approximately 80° C., the glass used in these electrodes tends to dissolve, leading to a rapid failure of the electrode.

In response to the above-described problems, various attempts have been made to construct pH electrodes having bodies composed of materials other than glass. One family of such alternative compositions for pH electrodes comprise certain metal oxide based ceramic materials, such as those described in U.S. Pat. No. 4,264,424, issued in the name of Niedrach on Apr. 28, 1981. Among these ceramics are zirconium oxide, thorium oxide, cerium oxide and lanthanum oxide, each of which is preferably stabilized by an admixture of another metal oxide such as yttrium oxide, strontium oxide, gadolinium oxide and calcium oxide, and all of which have been collectively referred to as oxygen ion conducting ceramics.

Among the internal conductive systems described in the latter patent are: a conventional silver halide coated silver wire immersed in an aqueous halide solution, a silver halide coated silver wire immersed in an electrolyte composed of a solid or molten oxyhalide salt, and a metallic conductor immersed in an electrolyte composed of a mixture of a metal and its oxide or a mixture of metal oxides.

Of these electrolyte systems, the liquid electrolytes are unsuitable for use with high temperature test solutions because of the internal pressures incident to the vaporization of the water in the electrolyte solution at such temperatures. The oxyhalide electrolyte systems are subject to similar problems, although at higher temperatures. Silver chlorate, for example, melts at 230° C. and decomposes with the release of oxygen at 270° C.; silver bromate and iodate melt and decompose at even lower temperatures. The contact of the resulting high temperature oxygen with the metal within the electrode can even be expected to give rise to a condition of rapid oxidation within the electrode. The metal oxide electrolyte systems, on the other hand, are undesirable because of the instabilities associated with the fact that the oxide ion has an activity that can change, particularly in the presence of metals having a number of different oxidation states.

Prior to the present invention, the presence of the above-mentioned types of electrolytes has been thought to be necessary because of the belief that oxygen had to be present in the material that contacts the inner surface of the ceramic material in order to provide a reference for the oxygen ions in that ceramic material. One basis for this belief is set forth in U.S. Pat. No. 3,619,381 issued in the name of Fitterer on Nov. 9, 1971. Thus, the use of electrode systems including metal oxide based ceramic materials has only partially solved the problems associated with the measurement of pH at high temperatures and pressures.

Various attempts have also been made to construct reference electrodes that provide the desired ionic continuity, but which do not have a leak structure in the usual, macroscopic sense. One such reference electrode is shown in U.S. Pat. No. 4,002,547, issued in the name of Neti et al. on Jan. 11, 1977. While such reference electrodes eliminate problems with the cross-contamination of the electrolyte solution and the test solution, they cannot be used with high temperature test solutions because of the previously described internal pressure problem. Other reference electrodes, such as those described in the above-cited Szonntagh patent, have solid electrolytes with cracked glass reference bodies and are therefore subject to the above-described temperature and pH limitations.

The foregoing remarks will be understood to be applicable, in part, to combination electrode systems, i.e., electrode systems in which the pH and reference electrodes are joined into a unitary physical structure. A combination electrode based on the use of liquid electrolytes for the pH and reference electrodes is shown, for example, in U.S. Pat. No. 4,128,468 issued in the name of Bukamier on Dec. 5, 1978. Combination electrodes based on the use of solid electrolytes are shown in the above-cited Butler and Szonntagh patents.

SUMMARY OF THE INVENTION

In accordance with the present invention there is provided an improved electrode system which is capable of accurately measuring the pH of high temperature test solutions and which is not subject to any of the above-described problems with glass electrodes, liquid filled electrodes, or metal oxide based ceramic electrodes having oxygen containing electrolytes.

The present invention is based in part on the discovery that, contrary to past belief, metal oxide based ceramic pH electrodes need not be used with oxygen containing electrolyte materials. On the contrary, it has been found that metal oxide based pH electrodes can be used with any of a variety of oxygen-free solid electrolyte materials such as a solid silver halide (other than fluoride), mixtures of a silver halide and metallic silver, mixtures of a silver halide and one or more alkali halides (other than fluoride) and one or more alkali halides, among others. In addition, it has been discovered that these solid electrolyte materials may have a uniform composition, i.e., may be implemented without the use of the multiple layers that characterize prior electrolyte systems. As a result of these discoveries, it is now possible to avoid the above-described problems with oxygen containing electrolyte materials.

The present invention is also based in part on the discovery that the body member of the reference electrode can be made from the same material as the body member of the pH electrode, i.e., a metal oxide based ceramic material. This discovery allows the bodies of the pH and reference electrodes to be fabricated at the same time, thereby laying a foundation for the manufacture of new types of combination electrode systems having a variety of desirable physical configurations.

The discovery that the same body material can be used for the pH and reference electrodes is, in turn, based on the discovery that the pH sensitivity of metal oxide based ceramics is a function of both their thickness and their porosity. At thicknesses in excess of 0.025 millimeters, for example, relatively porous zirconium oxide based ceramics (such as those formed from 300 mesh ceramic grains) exhibit the pH sensitive properties known to be associated therewith. At thicknesses of approximately 0.005 millimeters or less, however, porous zirconium oxide based ceramics lose this pH sensitivity. Alternatively, if the ceramic material is relatively imporous, i.e., exists in a relatively continuous glassy or crystalline form, it retains its pH sensitivity down to lower thicknesses, such as those in the range of 100 angstroms. At still lower thicknesses, however, even the continuous type of ceramic material will lose its pH sensitivity. As a result, it is possible, by using ceramic body members of differing thicknesses and/or porosities, to use the same material for both the pH and the reference electrodes. Particularly when used in conjunction with the discovery that oxygen-free solid electrolyte can be used in both types of electrodes, this allows both electrodes to be fabricated simultaneously, thereby reducing both the cost and the number of steps necessary to produce a workable electrode system.

In spite of the fact that the preferred embodiment of the invention contemplates the use of a metal oxide based ceramic for both the pH and the reference electrode, it is nevertheless possible to use the improved pH electrode of the present invention with reference electrodes constructed from a wide variety of other materials such as alkali metal salt or glass filled plastics, porous surfactant treated plastics, and other porous electrochemically inert materials such as aluminum and other metal oxides. These and other embodiments of the present invention are described in detail in the following description and drawings.

DESCRIPTION OF THE PREFERRED EMBODIMENTS

Figures 1, 1A, 2, 3:
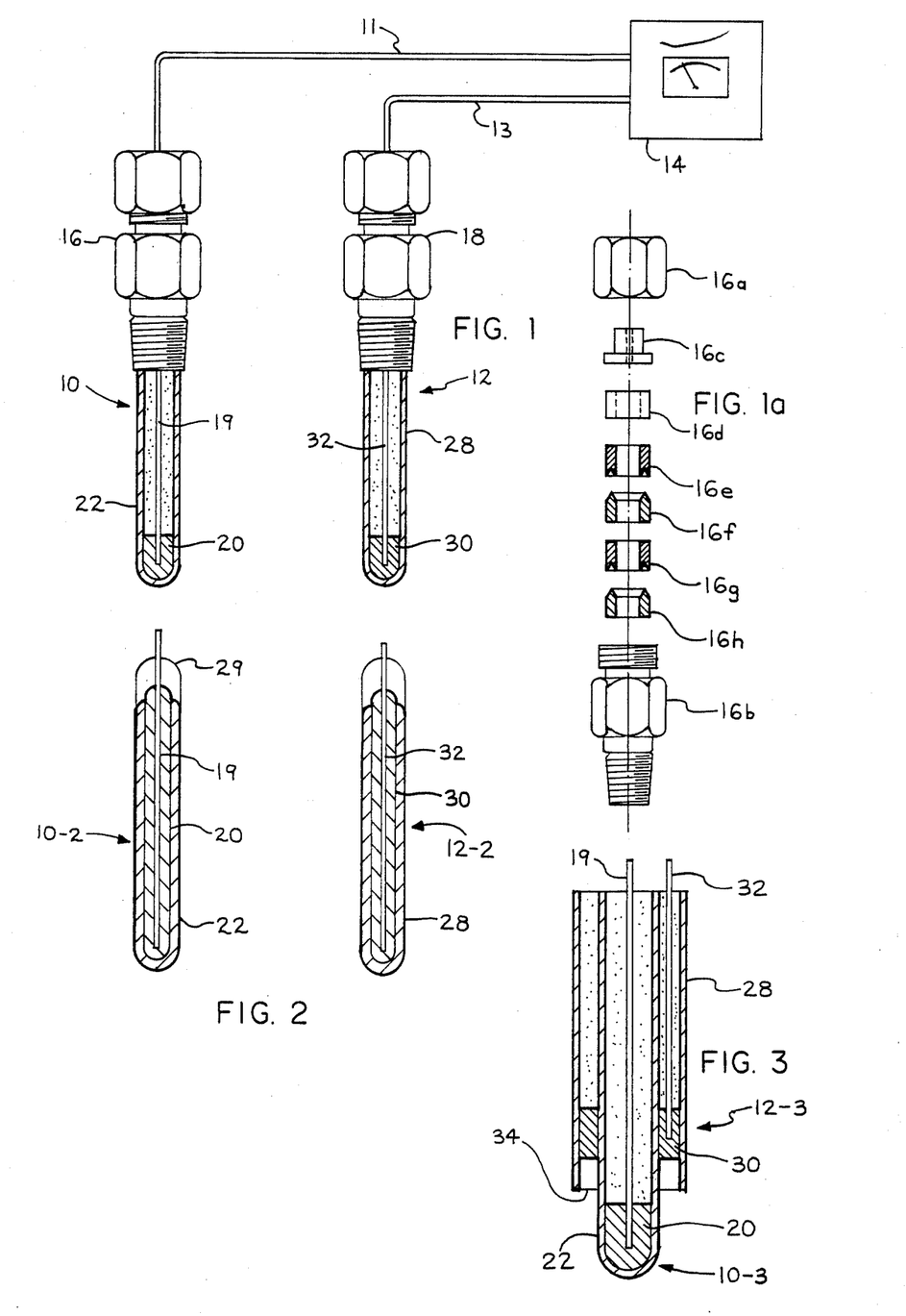
FIG. 1 is a partial cross-sectional view of an electrode system having separate pH and reference electrodes.
FIG. 1a is an exploded view of one of the connectors shown in FIG. 1.
FIG. 2 is a fragmentary cross-sectional view of an alternative embodiment of an electrode system having separate pH and reference electrodes.
FIGS. 3-5 are cross-sectional views of a variety of combination electrodes having generally tubular configurations.

Referring to FIG. 1, there is shown an embodiment of the electrode system of the invention which includes a pH electrode 10 and a reference electrode 12. Electrodes 10 and 12 are connected to a conventional high input impedance potential measuring instrument 14 through respective external conductors 11 and 13. During installation, electrodes 10 and 12 are preferably passed through openings in the wall of a vessel or chamber (not shown) containing the test solution and are sealed in place by high pressure connectors 16 and 18 which may each be of the type manufactured by Conax Corporation. Once these electrodes are installed and connected to instrument 14, the voltage between pH electrode 10 and reference electrode 12 will vary in the usual manner with the concentration of hydrogen ions in the test solution.

In the embodiment of FIG. 1, pH electrode 10 includes a generally tubular pH sensitive body member 22 that is composed of a metal oxide based ceramic material such as zirconium oxide (zirconia). This material is preferably stabilized by the addition of one or more other metal oxides; calcium oxide, yttrium oxide, or mixtures of rare earth oxides being most suitable for use with Zirconia. Other metal oxide based ceramic materials, such as cerium oxide that has been stabilized by an admixture of calcium or gadolinium oxides, are also usable. A fuller list of the subject type of metal oxide based ceramics, and their stabilizing materials, is set forth in the above-cited U.S. Pat. No. 3,619,381, which is hereby incorporated herein by reference.

In a first embodiment, pH sensing member 22 is composed of a relatively porous zirconia based ceramic material having a thickness greater than approximately 0.025 millimeters and less than approximately 3 millimeters. The lower one of these thickness limits represents the onset of reliable pH sensing characteristics in the ceramic material, while the upper of these thickness limits represents the thickness above which the impedance of the ceramic material increases without any compensating benefit. As used herein, the term "relatively porous" will be understood to include porosities in the range resulting from the use of conventional ceramic fabrication processes and ordinary powdered ceramic starting materials. As a specific example, the use of powdered zirconia having a grain size corresponding to approximately 300 mesh is desirable and results in a pore size in the several micron range.

pH sensing member 22 may also, however, be composed of a relatively imporous zirconia based ceramic material if the thickness thereof is substantially less than that described above. If, for example, the ceramic material is substantially continuous, i.e., in a glassy or crystalline state, the thickness of at least the active portion of member 22 may be as low as approximately 100 angstroms. Naturally, greater thicknesses may also be used, although the impedance of the electrode will be correspondingly increased. It will be understood that similar thickness limits ar applicable to relatively porous and imporous forms of the other metal oxide based ceramics mentioned above.

Included within pH sensitive member 22 is a body 20 of an electrolyte material which is in intimate electrical contact with the inner (non-solution) surface of member 22. This electrolyte material may have any of a variety of compositions which will be described more fully presently, and may be introduced into member 22 in any of a variety of ways that will also be described. Immersed in electrolyte body 20 is a metallic conductor 19, which is preferably composed of silver, platinum, gold, rhodium, iridium, palladium, tantalum or mixtures thereof, which couples electrolyte body 20 to external conductor 11. Also usable for conductor 19, although it is not a metallic conductor, is carbon, preferably in vitreous (glassy) form. As used herein, the term "electrolyte" will be understood to include all of the material lying between the central conductor of an electrode and the body member that is associated therewith.

It will be understood that body 20 may, but need not, fill the entire interior of member 22. It may instead cover only a selected portion thereof, which portion may then be regarded as the active portion of the electrode. If body 20 fills less than the entire interior of member 22, however, it is preferred that any open space above body 20 be filled with a suitable electrochemically inert potting material to seal the same and improve the resistance of the electrode to external pressure. One such potting material is that sold under the designation Ceramapot-576 by Aremco Products, Inc.

In spite of the past belief that oxygen must be present in the solid electrolytes used in ceramic pH electrodes, it has been discovered that it is not only possible but also desirable to use oxygen-free solid electrolytes with ceramic pH electrodes. This discovery is particularly surprising in view of the common characterization of metal oxide based ceramics as "oxygen ion conducting" ceramics, and in view of the belief that oxygen must be present in order to provide an oxygen reference for the ceramic material. As a result of this discovery, there is made possible a wide range of ceramic pH electrodes having solid oxygen-free electrolyte systems which have desirable characteristics from an operational as well as a manufacturing standpoint.

Among the solid electrolyte systems which are preferred for use in pH electrode 10 are: (a) a silver halide, other than fluoride, (b) mixtures of silver halides, other than fluoride, (c) a mixture of a silver halide, other than fluoride, with finely divided metallic silver, (d) a mixture of a silver halide, other than fluoride, and one or more alkali halides, other than fluoride, (e) one or more alkali halides, other than fluoride, and (f) carbon. Because of their solidity, these electrolyte materials contribute to the ability of the electrode to withstand high temperatures and pressures. In addition, because of their uniform composition, these electrolytes can be introduced into body member 22 in a single step, rather than in the series of steps necessary to produce known solid electrolyte systems.

Another electrolyte composition which may be used in pH electrode 10 in some applications, although its use is not preferred, is a composition including a dehydrated alkali silicate that contains one or more alkali halides, other than fluoride. Sodium silicate in the form of a "water glass" solution containing potassium chloride may, for example, be poured into member 22 and thereafter dehydrated by the application of heat to convert the solution to a solid mass. Electrolyte systems of this type are described in greater detail in my copending application Ser. No. 163,112, the disclosure of which is hereby incorporated herein by reference. Electrolyte systems of this type are not preferred because they contain oxygen. This oxygen content is less objectionable than that of other oxygen containing compounds, however, because of the nature of the silicon-oxygen bond in alkali silicate compounds.

In most cases the use of an electrolyte having a mixed composition is preferred because of the opportunity which the mixture provides to change the asymmetry potential of the electrode by varying the proportions of the ingredients of the electrolyte. In electrolytes composed of metallic silver and silver chloride, for example, a mixture in which the metallic silver comprises 40% by weight of the total will yield an approximately zero volt asymmetry potential. On the other hand, a reduction of the silver content to approximately 15% by weight will result in an asymmetry potential of approximately −200 millivolts. Conversely, positive asymmetry potentials can be produced by increasing the silver content to above 40% by weight.

The above-described solid electrolytes may be introduced into member 22 in any of a variety of ways. Electrolyte 20 may, for example, be poured into member 22 in flowable powdered form, have conductor 19 inserted therein and thereafter be compressed in place until electrolyte 20 is converted into a relatively solid mass. Electrolyte 20 may also be compressed around conductor 19 as a pellet, before insertion into member 22, and thereafter be re-compressed to assure a good electrical contact with member 22. It is also possible to introduce electrolyte body 20 into member 22 by pouring the same in wet or dry flowable form, inserting conductor 19, and thereafter heating member 22 until the electrolyte is converted into a solid mass. Still other ways of producing electrolyte body 20 include the introduction of the electrolyte in the form of a fluid slurry having a vaporizable component which can later be driven off by the addition of heat. It will be understood that the present invention contemplates all such ways for introducing electrolyte body 20 into pH electrode 10.

Reference electrode 12 has generally the same configuration as pH electrode 10. More particularly, reference electrode 10 includes a reference body member 28, an electrolyte body 30, and an internal conductor 32. The latter conductor, which is preferably composed of silver or other noble metal, is immersed in electrolyte body 30 to establish contact between member 28 and external conductor 13. As was the case with electrode 10, any open space within member 28 is preferably filled with a suitable electrochemically inert potting compound to improve the resistance thereof to external pressure.

In accordance with one feature of the present invention, it has been found that contrary to the common practice of providing reference electrodes with aqueous electrolyte solutions of, for example, buffered potassium chloride in which is immersed a silver chloride coated silver wire, or of providing a dry buffered potassium chloride layer surrounding a silver chloride coated silver wire, electrolyte 30 may comprise a uniform dry solid body having any one of the previously described compositions, except those containing alkali silicates or carbon. This uniformity is significant because it allows a reference electrode to be constructed without the above-mentioned additional electrolyte layer, thereby reducing the process of coupling the internal conductor to the ceramic member to a single step. In addition, the similarity of the electrolytes of the pH and reference electrodes is significant, in the context of the present invention, since it allows the internal structure of the reference electrode to parallel that of the pH electrode, thereby facilitating the simultaneous fabrication of the combination electrode systems which will be described hereinafter.

In one form of the preferred embodiment, reference member 28 may be constructed from the same relatively porous metal oxide based ceramic as pH sensitive member 22, provided that reference member 28 has a thickness of less than approximately 0.005 millimeters. This use of the same material for the reference and pH electrode bodies is possible because it has been found that relatively porous stabilized metal oxide based ceramics lose their pH sensitive properties when the thickness thereof is reduced to a value in the just stated range. This similarity of compositions in members 22 and 28 is preferred because it facilitates the simultaneous fabrication of the pH and reference electrodes in configurations which are not feasible with the use of dissimilar materials for members 22 and 28.

In another form of the preferred embodiment, reference member 28 may be constructed from the same relatively imporous ceramic material as pH sensitive member 22, provided that reference member 28 has a thickness in the range of approximately 10 to 50 angstroms. This is possible because it has been found that the pH sensitivity of the metal oxide based ceramic materials is a function of their thickness in relatively imporous forms as well as in relatively porous forms.

Reference member 28 may also have the same composition and thickness as pH sensitive member 22, provided that member 28 has, or is made to have, a greater porosity than member 22. If, for example, members 22 and 28 are both composed of relatively porous or imporous metal oxide based ceramic material having equal thicknesses, pH insensitive properties may be induced in the reference member by thereafter increasing the porosity thereof. One process by which this may be accomplished includes the directing of a laser beam, from for example a $CO_2$ or YAG laser, in a scanning pattern across the outer surface of the reference member. The frequency of the laser radiation is not critical. This laser beam, which may have a peak total power of as little as one watt, effectively "blasts" from the surface of the reference member a sufficient quantity of the ceramic material to produce therein irregularities that increase the porosity of the reference member. Significantly, the laser scanning need not cover the entire outer surface of the reference member; it is sufficient that an appreciable portion of the surface area thereof be covered with a set of laser inscribed lines or dots. It will be understood that electron beams may be used in place of laser beams with similar results.

In view of the foregoing, it will be seen that the ceramic material contemplated by the present invention can serve either as a pH or as a reference member, depending upon the relationship of the porosity and thickness thereof.

While the use of a reference member which has the same composition as the pH sensitive member is preferred, a variety of filled plastic materials have also been found to be usable in fabricating the reference member. These plastic materials are not preferred because the use of each involves some sacrifice in the maximum temperature at which the electrode system may be operated. Various ones of these plastic reference member materials, together with their approximate maximum operating temperatures, include: polytetrafluoroethylene (TFE) $-320°$ C., polyfluorinated ethylene propylene (FEP) $-280°$ C., polychloro-trifluoroethylene $-300°$ C., polyvinylidene fluoride (PVF) $-220°$ C., acrylic butadiene styrene (ABS) $-160°$ C., polyphenylene sulfide $-320°$ C., polyvinyl chloride (PVC) $-150°$ C., polymethyl methacylate $-150°$ C. and nylon $-290°$ C. A representative range of thicknesses for such plastic reference members is from 0.5 to 2.5 mm.

Among the possible filling materials for these plastics are (a) glass powder or fibers, (b) quartz powder or fibers, (c) an alkali halide, other than fluoride, (d) an alkali metal nitrate, and (e) an alkali metal sulfate. In all cases, the blending and molding of the above filled plastic materials may be accomplished using conventional techniques. Reference member 28 may also be fabricated from a variety of electrochemically inert porous materials including metal oxides, such as aluminum oxide, and porous unfilled Teflon, the latter preferably being treated with a surfactant such as those sold under the names Tergitol 15-S-9 by Union Carbide and Triton X-100 by Rohm and Haas.

Because of the high temperatures and pressures which the electrode system of the invention is intended to accommodate, such as temperatures up to and even exceeding 374.2° C. (the critical point of water) and pressures at least as high as 1400 psi, care must be exercised in the choice of the sealing structures and materials used therewith. One suitable sealing structure is shown in exploded form in FIG. 1a, which illustrates the preferred internal structure of pressure connector 16. As shown in FIG. 1a, connector 16 includes upper and lower threaded connector sections 16a and 16b which may be of the type manufactured by Conax Corporation, a pressure plate 16c which may be composed of Torlon, a top ring 16d which may be composed of TFE, and one or more pairs of interlocking sealing rings such as 16e and 16f, and 16g and 16h. Preferably one of each of these pairs of sealing rings is composed of stainless steel and the other is composed of zirconia filled TFE. The latter material, which may include from 15 to 45% by weight of zirconia, has been found to have surprisingly desirable sealing properties, such as high dimensional stability in the presence of repeated thermal cycling, and its use in high temperature electrode systems is regarded as a secondary feature of the present invention.

Because empty spaces will not ordinarily exist within pH electrode 10 and reference electrode 12, the pressure at which they can be used is less a matter of their internal pressure resistance than it is a matter of the maximum pressure difference that can be withstood by connectors 16 and 18. This is because electrodes 10 and 12 will ordinarily be maintained in contact with a pressurized test solution by the action of the tapered threads on the ends of connectors 16 and 18, and because their use in this manner causes the difference between the pressure of the test solution and ambient pressure to appear across the pairs of sealing rings within connectors 16 and 18. The true maximum value of this pressure difference is uncertain, but is believed to be significantly in excess of 1400 psi, the latter being the maximum pressure at which the embodiment of FIG. 1 has been actually tested.

With respect to the temperature limits within which the electrode system of the invention may be used, these are quite broad and extend well beyond the range within which the use of glass or liquid filled electrodes is possible. The preferred lower limit of this temperature range is approximately 75° C., the latter being the temperature at which the impedance of the ceramic material increases substantially and becomes increasingly nonlinear. The pH electrode of the invention may, however, be used even at temperatures below 75° C. if the potentiometric measuring instrument 14 is provided with a microcomputer having a look-up table by which these impedances and nonlinearities can be taken into account. The absolute upper limit of this temperature range is related to the temperatures at which the internal conductor or the electrolyte used therein begin to soften or decompose. In a more practical sense, however, the maximum operating temperature for the electrode system of the invention may be regarded as the critical temperature of the test solution, i.e., the temperature above which differences between the liquid and gaseous phases of the test solution disappear. For water, for example, this temperature is approximately 374° C., a temperature which the preferred embodiment of the electrode system of the invention may accommodate without difficulty. Even higher temperatures can be withstood, however, even though the resulting readings may be subject to differing interpretations.

In view of the foregoing, it will be seen that the electrode system of the invention will operate over an extremely wide range of temperatures and pressures, the extreme limits of which are defined less by the characteristics of the electrode system than by those of the connectors and materials with which the electrode system is used.

The embodiment of FIG. 1 represents an electrode system comprising two separate or stand-alone electrodes each of which is fabricated in the usual manner, i.e., by the addition of internal elements to the outer member or, differently stated, from the outside-in. The electrode system of the present invention can, however, also be fabricated in the reverse order, i.e., by the addition of layers to the innermost member or from the inside-out. Referring to FIG. 2, for example, there is shown an electrode system which is generally similar to that of FIG. 1, like functioning parts being similarly numbered, but which is manufactured by the addition of successive layers over internal conductors 19 and 32.

More particularly, pH electrode 10-2 of FIG. 2 is manufactured by depositing solid electrolyte body 20 as a layer over conductor 19 as, for example, by dipping conductor 19 in an adherent electrolyte slurry and thereafter heating it, or by compressing a dry electrolyte powder therearound. pH sensitive member 22 may thereafter be added by depositing a layer of ceramic material around electrolyte body 20 by RF sputtering, plasma spraying or other suitable process. Once pH sensitive layer 22 has been deposited, it may be machined to the desired thickness by, for example, grinding. pH electrode 10 may then be mounted in a suitable connector such as that shown in FIG. 1, this connector being omitted from FIG. 2 for the sake of simplicity.

In order to prevent the short-circuiting of electrolyte body 20, it is desirable that member 22 not extend over the upper end of electrolyte layer 20. If the ends of layers 20 and 22 extend far enough into connector 16, no sealant need be applied to maintain the isolation of conductor 19 from layer 22. If this is not the case, conductor 19 may be isolated from layer 22 by the deposition of a sealant body 29 composed of a suitable electrochemically inert material which can withstand the temperatures to which it will be exposed. One such material is the previously described zirconia filled TFE.

Similarly, reference electrode 12-2 of FIG. 2 may be made by applying successive layers over internal conductor 32. Electrolyte body 30 may, for example, be applied over conductor 32 by dipping, by compression molding or the heating of powders or slurries, in the manner previously described. Reference member 28 may then be applied as a layer over body 30 in any manner that is compatible with the composition thereof. If, for example, reference member 28 comprises a zirconia based ceramic, the ceramic layer may be added by RF sputtering, plasma spraying or other suitable process. If, on the other hand, reference member 28 comprises one of the previously described filled plastic materials, body member 28 may be applied by molding and/or sintering the plastic in the usual manner.

In view of the similarities of the embodiments of FIGS. 2-8 to that of FIG. 1, and in order to avoid unnecessary repetition, the indicia used for the pH and reference electrodes shown in FIGS. 2-8 will be the same as those used in FIG. 1, except for the addition of a postscript which will correspond to the number of the Figure in which the electrode is shown. In addition, the indicia used for the components of the electrodes of FIGS. 2-8 will be the same as those used for the corresponding components of the embodiment of FIG. 1, in spite of non-material differences in size and shape.

The electrode system of the present invention may also be practiced by joining the pH and reference electrodes to form a combination electrode assembly having any of a variety of configurations. Selected representative ones of these configurations are shown in FIGS. 3-8 which will now be described.

Referring to FIG. 3, there is shown an embodiment of the invention in which the pH and reference electrodes are joined to form a combination electrode having a generally tubular configuration. More particularly, the embodiment of FIG. 3 includes a pH electrode 10-3 which may be identical to pH electrode 10 of FIG. 1, and a reference electrode 12-3 that includes a tubular member 28 which fits over and is concentric with pH sensitive member 22. Reference member 28 may have any of the thicknesses, porosities and compositions described previously in connection with FIG. 1. In addition, reference electrode 12-3 includes a dry solid electrolyte body 30 and an internal conductor 32 which may each also have any of the compositions described previously in connection with FIG. 1.

In order to facilitate the assembly of the combination electrode of FIG. 3, an annular spacer 34 composed of a suitable electrochemically inert material may be placed over the end of pH sensitive member 22 to aid is the orientation of reference member 28. One spacer 34 and member 28 are in place, electrolyte body 30 and conductor 32 may then be added in any of the previously described ways to complete reference electrode 12-3. Any empty space above electrolyte body 30 in reference electrode 12-3 as well as any empty space within pH electrode 10-3 may then be filled with a suitable potting compound.

Figure 4:
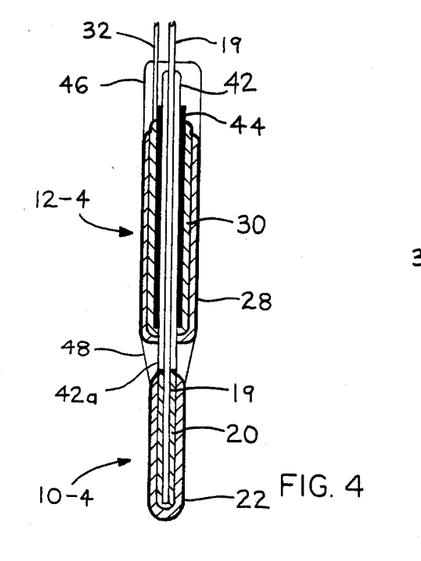

Referring to FIG. 4, there is shown another generally tubular combination electrode system that is suitable for use in practicing the present invention. The embodiment of FIG. 4 is generally similar to that of FIG. 3, but differs therefrom in two respects. The first respect is that in the embodiment of FIG. 4 the pH electrode 10-4 is similar to pH electrode 10-2 of FIG. 2, while in FIG. 3 the pH electrode 10-3 is similar to pH electrode 10 of FIG. 1. As a result of this difference, the open space that is shown within the pH electrodes of FIGS. 1 and 3 may be eliminated, resulting in a combination electrode having a substantially smaller diameter.

A second respect in which the embodiment of FIG. 4 differs from that of FIG. 3 is that in FIG. 4 pH electrode 10-4 is located at the end of the electrode assembly and is separated from the reference electrode 12-4 thereof by a space 42a that is defined by the projecting end of a tubular insulating spacer 42. Insulating spacer 42 of FIG. 4 is, in part, analogous to spacer 34 of FIG. 3, and serves to separate and isolate pH sensitive and reference members 22 and 28. In FIG. 4, however, spacer 42 also serves as the foundation upon which reference electrode 12-4 may be deposited, from the inside-out in a succession of layers. More particularly, spacer 42 may be overlain by a metallization layer 44 to which conductor 32 may be connected. Electrolyte layer 30 and reference member 28 may then be deposited in succession to complete the reference electrode structure. The exposed ends of layers 20, 22, and 30 and 28 may then be sealed against contact with the test solution by bodies 46 and 48 of a suitable sealant compound such as the previously mentioned zirconia filled TFE or Cermapot-576. It will be understood that, in high pressure applications, the embodiment of FIG. 4 should be used with a high pressure connector of the type shown in FIG. 1.

Figure 5A:
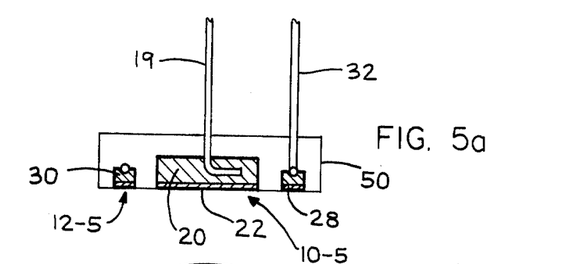
Figure 5B:
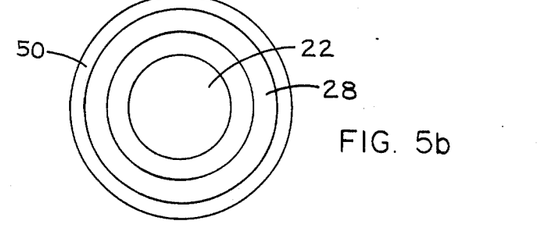

Referring to FIGS. 5a and b, there are shown two views of a generally tubular combination electrode which has a reduced longitudinal dimension. More particularly, the embodiment of FIG. 5 includes a generally disc shaped pH sensitive member 22 which is surrounded by a generally annular reference member 28 which is concentric therewith, as shown in FIG. 5b. Both of these members may have any of the thicknesses, porosities and compositions described in connection with their counterparts in FIGS. 1-4. Members 22 and 28 are preferably mounted in a suitable electrochemically inert sealant matrix 50 which may comprise one of the above-mentioned compounds, among others. As shown in FIG. 5a, pH sensitive and reference members 22 and 28 are coupled to their respective internal conductors 19 and 32 by respective electrolyte bodies 20 and 30, each of which may have an appropriate one of the previously described compositions. In spite of its different physical configuration, the electrode system of FIG. 5 operates in the same manner as the embodiments of FIGS. 1-4 and accomplishes the same result.

The electrode of FIG. 5 may be produced in one of two ways. Firstly, the pH electrode and reference electrode subassemblies thereof may be preassembled and inserted into a mold with their active (outer) surfaces facing the mold. Sealan matrix 50 may then be molded thereover. Upon removal from the mold, any adherent sealant may then be removed from the active surfaces of members 22 and 28. Alternatively, sealant matrix 50 may be preformed in the shape shown, the electrolyte bodies, conductors and body members being added later, in succession, until the structure is completed. If the latter approach is used, the edges of members 22 and 28 are preferably provided with a suitable temperature resistant cement before final insertion into matrix 50. One such suitable cement comprises a polyimide adhesive such as that sold under the designation SA300 by Zirmex, Inc.

Figures 6A, 6B:
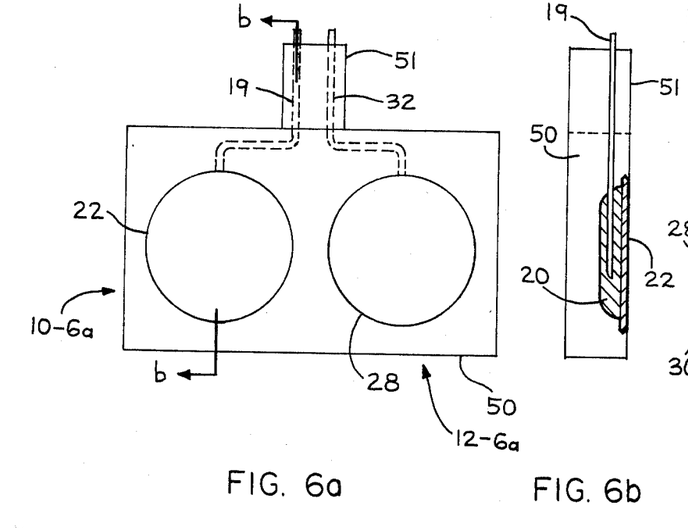
FIGS. 6a-c, 7a-c and 8 are cross-sectional views of a variety of combination electrodes having generally planar configurations.

Referring to FIGS. 6a and b, there are shown front and cross-sectional views of an embodiment of a combination electrode having a generally planar configuration. As shown in in the front view of FIG. 6a, the combination electrode includes a pH electrode portion 10-6 having a disc shaped pH sensitive member 22, and a reference electrode portion 12-6 having a disc shaped reference member 28. These body members are mounted in side-by-side relationship in a sealant matrix 50 of the type described in connection with FIG. 5. As shown in the cross-sectional view of FIG. 6b, pH sensitive member 22 overlies the solid electrolyte body 20 in which conductor 19 is imbedded. A similar arrangement (not shown) will be understood to exist for reference member 28. The compositions and methods of assembling these electrodes may be as described previously in connection with FIGS. 1-5.

One advantageous respect in which the embodiment of FIG. 6 differs from that of FIG. 5 is that, in the embodiment of FIG. 6, sealant matrix 50 is provided with a cylindrical post 51 through which conductors 19 and 32 are preferably routed. This post, which may (but need not) be integral with matrix 50, serves not only as a convenient mounting element, but also as a neck by means of which the combination electrode may form a seal with a connector such as 16 in FIG. 1. In the event that post 51 is non-integral with matrix 50, it is preferably composed of a chemically resistant metal, such as stainless steel.

As in the case of FIG. 5, the embodiment of FIG. 6 may be produced either from the inside-out or from the outside-in. Because of the side-by-side relationship of members 22 and 28, however, the molding of sealant matrix 50 around the pre-assembled electrode subassemblies (outside-in fabrication) is preferred. One reason is that this sequence provides a convenient opportunity for the attachment of post 51. Another reason is that, during the grinding off of excess sealant from the active outer surfaces of members 22 and 28, a portion of the thickness of member 28 can also be ground off. This fact can be utilized, in embodiments in which both ceramic members have similar porosities to in effect induce pH insensitive (reference electrode) properties in a ceramic member that was originally thick enough to have pH sensitive properties. Either of these processes, in turn, allows the pH and reference members to be produced from a single antecedent structure, thereby reducing the cost of manufacture.

Figure 6C:
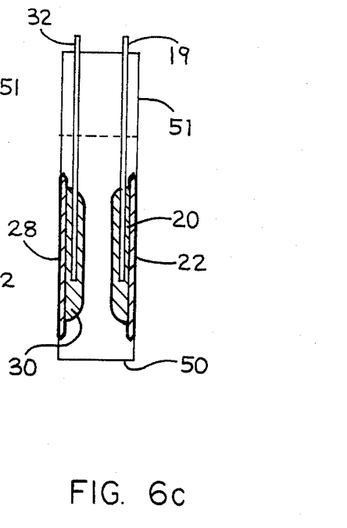

In addition to being constructed in the side-by-side configuration shown in FIGS. 6a and b, the combination electrode of FIG. 6 may also be constructed in a back-to-baCk configuration. A cross-sectional view of a combination electrode of the latter type is shown in FIG. 6c. Because of the close similarity between the electrode system of FIGS. 6a and b and that of FIG. 6c, the latter will not be described in detail herein.

Figure 7A:
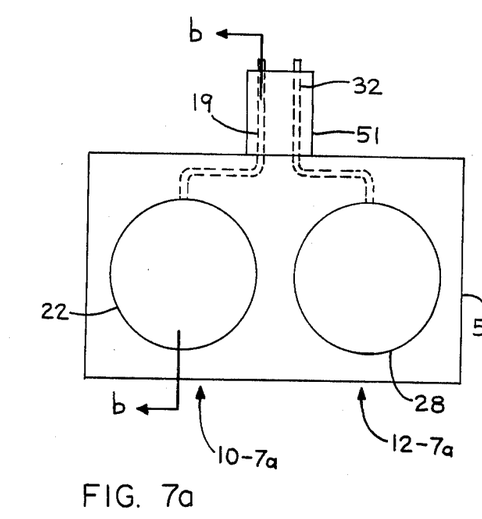
Figures 7B, 7C:
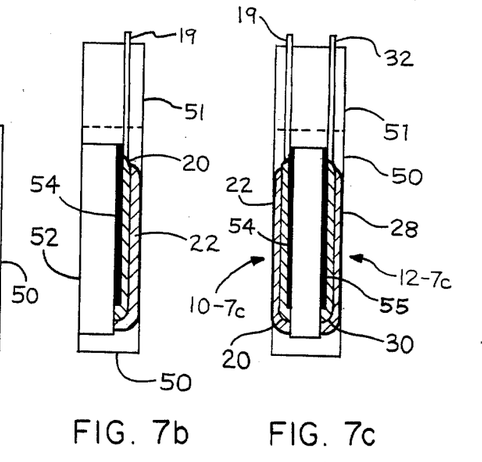

Referring to FIGS. 7a and b, there is shown another embodiment of a generally planar combination electrode. The embodiment of FIG. 7 is similar to that of FIG. 6, but differs therefrom primarily in that the embodiment of FIG. 7 includes an insulating substrate 52, shown in FIG. 7b, upon which the electrodes may be built up, from the inside-out, by the use of thick or thin film deposition techniques. A metallization layer 54 which has been vapor deposited directly on substrate 52 may, for example, serve as an extension of internal conductor 19. Solid electrolyte body 20 can then be deposited thereover in any of the previously described ways. pH sensitive member 22 may then be deposited over body 20, by RF sputtering, plasma spraying, etc., to complete pH electrode 10-7. The reference electrode portion 12-7 (not shown in cross-section) may be made in exactly the same manner and at the same time. Once both electrodes are in place, sealant matrix 50 may be applied as before, post 51 being formed or attached at that time.

After the sealant matrix 50 is dry, any excess sealant covering the active outer surfaces of members 22 and 28 may be ground off to assure a good contact with the test solution. As described in connection with FIG. 6, if the pH sensitive and reference members have the same composition, both members can be deposited simultaneously. One of the electrodes may then be converted to a reference electrode by one of the previously described conversion processes.

It will be understood that the embodiment of FIG. 7 may also be constructed with the pH and reference electrodes located on opposite sides of substrate 52. A cross-sectional view of an electrode system having the latter configuration is shown in FIG. 7c.

Figure 8:
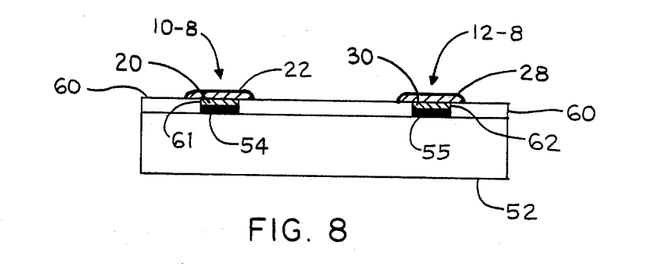

Still another embodiment of a combination electrode having a planar configuration is shown in cross-section in FIG. 8. The embodiment of FIG. 8 is generally similar to that of FIG. 7, like functioning parts being similar numbered. The principal difference between the embodiments of FIGS. 7 and 8 is that, in the embodiment of FIG. 8, the metallization layer 54 of pH electrode 10-8 and the metallization layer 55 of reference electrode 12-8 both lie on insulating substrate 52 under a silicon dioxide insulating layer 60. Electrolyte bodies 20 and 30 make contact with these metallization layers through respective windows 61 and 62 which are opened through silicon dioxide layer 60 in the usual manner. Once the electrolyte bodies have been deposited, the pH sensitive and reference layers 22 and 28 may then be deposited in any of the previously described ways. Naturally, the latter step is most easily accomplished if members 22 and 28 have the same composition.

One advantage of the embodiment of FIG. 8 is that the use of insulating layer 60 is sufficiently effective in insulating metallization layers 54 and 55 that no all-enveloping sealing matrix is necessary; sealant need be applied only at the points at which metallization layers emerge from under insulating layer 60 to make contact with the leads that will connect them to instrument 14. Another advantage of the embodiment of FIG. 8 is that it may be made, many copies at a time, in much the same manner that transistors are made. This, in turn, allows the manufacture of extremely small combination electrodes, the only real size limitations being those imposed by the thiokness requirements of ceramic layers 22 and 28. As a result, the combination electrode of FIG. 8 can be used in applications involving very small quantities of test solution, and in applications in which the electrode system must produce little or no disruption of the flow of the test solution.

In view of the foregoing, it will be seen that an electrode system constructed in accordance with the present invention makes possible pH measurements at temperatures and pressures well beyond those possible through the use of previously available pH sensitive and electrolyte materials. Moreover, these changes in materials allows single and combination electrodes to be manufactured in a variety of configurations not possible through the use of previously available materials, thereby greatly reducing the cost of the electrode as well as extending its performance.

What is claimed is:

1. A high temperature electrode system for indicating the pH of a test solution, the combination comprising:
   a. a pH electrode including:
      i. a pH sensitive member composed of a metal oxide based ceramic, having an outer surface and an inner surface, and said outer surface disposed for direct contact with said test solution;
      ii. a first oxygen-free solid electrolyte body in the pH sensitive member for direct contact with said inner surface of said pH sensitive member,
      iii. a first metal conductor in electrical contact with said first electrolyte body, and means on said first metal conductor for connecting said pH electrode to an instrument for measuring electrical potential,
   b. a reference electrode including:
      i. a reference member having, an outer surface and an inner surface, said outer surface disposed for direct contact with said test solution;
      ii. said reference member has the same composition and porosity as the pH sensitive member and has a thickness in the range of 10 to 50 Angstroms,
      iii. a second oxygen-free solid electrolyte body in the reference member for direct contact with said inner surface of said reference member, and said second oxygen-free solid electrolyte body composed of a material selected from the group consisting of: a silver halide other than fluorides, mixtures of silver halides other than fluorides, mixtures of a silver halide other than fluoride and metallic silver, mixtures of a silver halide other than flouride and one or more alkali halide other than fluoride, an alkali halide other than fluoride, and mixtures of alkali halide other than fluorides, and
      iv. a second metal conductor in electrical contact with said second electrolyte body, and means on said metal conductor for connecting the reference electrode to an instrument for measuring electrical potential.

* * * * *